United States Patent
Doering

(10) Patent No.: US 10,603,257 B2
(45) Date of Patent: *Mar. 31, 2020

(54) EMULSIFYING SYSTEM FOR MICROEMULSIONS

(71) Applicant: Henkel AG & Co. KGaA, Duesseldorf (DE)

(72) Inventor: Thomas Doering, Dormagen (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/102,496

(22) Filed: Aug. 13, 2018

(65) Prior Publication Data

US 2019/0060183 A1 Feb. 28, 2019

(30) Foreign Application Priority Data

Aug. 24, 2017 (DE) .................. 10 2017 214 798

(51) Int. Cl.
| | |
|---|---|
| *A61K 8/06* | (2006.01) |
| *A61K 8/26* | (2006.01) |
| *A61K 8/34* | (2006.01) |
| *A61K 8/37* | (2006.01) |
| *A61K 8/86* | (2006.01) |
| *A61K 8/87* | (2006.01) |
| *A61K 8/92* | (2006.01) |
| *A61Q 15/00* | (2006.01) |

(52) U.S. Cl.
CPC .............. *A61K 8/068* (2013.01); *A61K 8/062* (2013.01); *A61K 8/26* (2013.01); *A61K 8/345* (2013.01); *A61K 8/37* (2013.01); *A61K 8/86* (2013.01); *A61K 8/87* (2013.01); *A61K 8/922* (2013.01); *A61Q 15/00* (2013.01); *A61K 2800/21* (2013.01); *A61K 2800/591* (2013.01)

(58) Field of Classification Search
CPC .......... A61K 8/068; A61K 8/062; A61K 8/26; A61K 8/345; A61K 8/37; A61K 8/86; A61K 8/87; A61K 8/922; A61K 2800/21; A61K 2800/591; A61Q 15/00

See application file for complete search history.

(56) References Cited

U.S. PATENT DOCUMENTS

| | | | |
|---|---|---|---|
| 2,571,030 | A | 10/1951 | Govett |
| 3,887,692 | A | 6/1975 | Gilman |
| 3,904,741 | A | 9/1975 | Jones et al. |
| 4,017,599 | A | 4/1977 | Rubino |
| 4,359,456 | A | 11/1982 | Gosling et al. |
| 4,775,528 | A | 10/1988 | Callaghan et al. |
| 6,010,688 | A | 1/2000 | Shen |
| 6,436,381 | B1 | 8/2002 | Carrillo et al. |
| 6,649,152 | B2 | 11/2003 | Carrillo et al. |
| 6,923,852 | B2 | 8/2005 | Vrotsos |
| 8,034,755 | B2 * | 10/2011 | Kawano .................. A61K 8/31 510/130 |
| 2003/0103921 | A1 | 6/2003 | Brucks |
| 2003/0124158 | A1 * | 7/2003 | Heidenfelder ......... A61K 8/044 424/401 |
| 2004/0126345 | A1 | 7/2004 | McNamara |
| 2004/0247547 | A1 * | 12/2004 | Kux ....................... A61K 8/042 424/65 |
| 2005/0009717 | A1 | 1/2005 | Lukenbach |
| 2007/0134191 | A1 | 6/2007 | Singer |
| 2011/0033413 | A1 * | 2/2011 | Kwetkat .............. A61K 8/0208 424/78.03 |
| 2017/0281517 | A1 * | 10/2017 | Doering ................. A61K 8/062 |

FOREIGN PATENT DOCUMENTS

| | | |
|---|---|---|
| EP | 0820758 A2 | 1/1998 |
| GB | 1347950 A | 2/1974 |
| GB | 2048229 A | 12/1980 |
| WO | 1996028132 A2 | 9/1996 |
| WO | 2000061083 A1 | 10/2000 |
| WO | 2016012327 A2 | 1/2016 |

\* cited by examiner

*Primary Examiner* — Shirley V Gembeh
(74) *Attorney, Agent, or Firm* — Lorenz & Kopf, LLP

(57) ABSTRACT

The present disclosure relates to antiperspirant and/or deodorizing cosmetic agent agents in the form of emulsions, which contain at least one non-ionic emulsifier a), wherein an ethoxylated, saturated, branched $C_{14}$-$C_{18}$ alcohol has an ethoxylation degree of from about 18 to about 22 ethylene oxide units, and at least one further non-ionic emulsifier b), wherein an ethoxylated, linear, mono-unsaturated $C_{16}$-$C_{20}$ alcohol has an ethoxylation degree of from about 18 to about 22 ethylene oxide units, wherein the weight ratio of the non-ionic emulsifier a) to the non-ionic emulsifier b) is from about 1.2:1 to about 4.0:1. The cosmetic agents as contemplated herein are optically transparent and have an improved storage stability, even under fluctuating temperatures.

20 Claims, No Drawings

EMULSIFYING SYSTEM FOR MICROEMULSIONS

CROSS-REFERENCE TO RELATED APPLICATION

This application claims priority to German Patent Application No. 10 2017 214 798.9, filed Aug. 24, 2017, which is incorporated herein by reference in its entirety.

TECHNICAL FIELD

The present disclosure relates to antiperspirant and/or deodorizing cosmetic agents in the form of emulsions, which contain a combination of selected O/W emulsifiers in a specific weight ratio. The cosmetic agents as contemplated herein are optically transparent and have an improved storage stability, even under fluctuating temperatures.

BACKGROUND

Washing, cleaning and care for the body are a basic human need and modern industry continuously attempts to meet these human needs in a variety of ways. Long-lasting elimination or at least reduction of the body odor and underarm wetness are especially important for daily hygiene.

Body odor is caused by the bacterial decomposition of the constituents of the initially odorless sweat. The decomposition products, which contribute significantly to the body odor, in particular to the axillary body odor, can be divided into three classes: short-chain $C_4$-$C_{10}$ fatty acids, which may be linear, branched, saturated and unsaturated (for example, isovaleric acid, 3M2H) constitute the first class, short-chain linear or branched sulfanyl alcohols constitute the second class, the third class includes various steroid hormones and their metabolic products (for example, 5-alpha androstenol and 5-α androstenone).

Body odor can therefore be combated by preventing the bacterial decomposition of the sweat. State-of-the-art antimicrobial substances are used to prevent the bacterial decomposition of the sweat. These reduce the number of sweat-decomposing bacteria on the skin by killing them and/or inhibiting the growth of these bacteria. Active substances are also known that reduce and/or prevent the formation of decomposition products by blocking bacterial enzymes. It is furthermore a commonly known fact that volatile decomposition products are absorbed by physical and/or chemical interaction, which avoids unpleasant body odor.

Moreover, body odor can be combated by preventing the perspiration of the body. Cosmetic antiperspirants from the prior art contain at least one antiperspirant salt. To achieve a high degree of sweat reduction, aluminum zirconium halides are preferably used in the prior art. The antiperspirant effect of these salts can be further improved by thermal treatment and the addition of ligands or phosphates, for example.

The transparent appearance of cosmetic agents is frequently desired by consumers. Cosmetic agents in the form of transparent emulsions are known. For transparent emulsions, the droplets distributed in the dispersed phase should have as small a mean particle diameter as possible, generally significantly below about 1000 nm, preferably below about 400 nm or even below about 200 nm.

Such agents of the prior art can generally lead to an impaired skin tolerance due to the high emulsifier content required to stabilize the emulsion. Furthermore, when such agents of the prior art are applied textile stains can form, which are perceived as undesirable by the consumer.

Cosmetic agents in the form of microemulsions that have a comparatively lower emulsifier content have therefore also already been developed. For example, WO96/28132 A2 discloses microemulsion gels as the basis for deodorizing or antiperspirant preparations, containing at least one polyethoxylated and/or polypropoxylated O/W emulsifier. WO00/61083 A1 discloses transparent microemulsions with about 2 or more non-ionic surfactants, of which one has an HLB value greater than about 10 and the other has an HLB value less than about 10.

Among other things, EP 820758 A2 deals with the stability of microemulsions and provides stable microemulsions, which contain a polyethoxylated and/or polypropoxylated O/W emulsifier, an oil component and a cationic surfactant, wherein the total quantity of emulsifier is about 2 wt. % or less.

However, the stability of microemulsions is often still in need of improvement, in particular when they are exposed to large temperature fluctuations, meaning that initially clear emulsions become cloudy over time. Even the addition of perfume oils cannot always guarantee the maintenance of a good level of transparency.

The present disclosure therefore addressed the problem of preparing cosmetic agents in the form of transparent microemulsions, in particular for deodorizing and/or antiperspirant preparations, which have a high storage stability under fluctuating temperatures. In the process, a good skin tolerance and a low residue formation, in particular on textiles, should preferably be ensured. Furthermore, these agents should also have an excellent antiperspirant and/or deodorizing effect.

Surprisingly, this problem was solved by the fact that, besides an oil component and an antiperspirant and/or deodorizing active ingredient, the cosmetic agent contains a combination of specific O/W emulsifiers in a specific weight ratio. Due to a low emulsifier concentration, a good skin tolerance can also be achieved.

BRIEF SUMMARY

Cosmetic agents are provided herein. In an embodiment, a cosmetic agent is provided in the form of an O/W emulsion. The cosmetic agent includes, in an aqueous cosmetically compatible carrier, a) at least one non-ionic emulsifier, b) at least one further non-ionic emulsifier, c) at least one antiperspirant and/or deodorizing active ingredient, and d) at least one oil component. The at least one non-ionic emulsifier a) includes an ethoxylated, saturated, branched $C_{14}$-$C_{18}$ alcohol having an ethoxylation degree of from about 18 to about 22 ethylene oxide units. The at least one further non-ionic emulsifier b) includes an ethoxylated, linear, mono-unsaturated $C_{16}$-$C_{20}$ alcohol having an ethoxylation degree of from about 18 to about 22 ethylene oxide units. The total quantity of emulsifiers in the cosmetic agent is from about 1.5 to about 8.0 wt. %, relative to the total weight of the cosmetic agent and the weight ratio of the non-ionic emulsifier a) to the non-ionic emulsifier b) is from about 1.2:1 to about 4.0:1.

In another embodiment, a cosmetic agent is provided in the form of an O/W emulsion. The cosmetic agent includes, in an aqueous cosmetically compatible carrier, at least one non-ionic emulsifier, at least one further non-ionic emulsifier, at least one antiperspirant and/or deodorizing active ingredient, at least one oil component, and at least one polyethylene glycol ether. The at least one non-ionic emulsifier includes an ethoxylated, saturated, branched $C_{14}$-$C_{18}$ alcohol having an ethoxylation degree of from about 18 to about 22 ethylene oxide units. The at least one further non-ionic emulsifier includes an ethoxylated, linear, mono-unsaturated $C_{16}$-$C_{20}$ alcohol having an ethoxylation degree of from about 18 to about 22 ethylene oxide units. The at least one polyethylene glycol ether is of the general formula R—O—(—CH$_2$—CH$_2$—O—)$_n$—R', wherein R and R' independently denote branched or unbranched alkyl, aryl or alkenyl radicals and n is an integer from about 100 to about 400. When present, the at least one antiperspirant active ingredient is present in a total quantity of from about 10 to about 20 wt. %, relative to the total weight of the cosmetic agent. When present, the at least one deodorizing active ingredient is present in a total quantity of from about 0.0001 to about 40 wt. %, relative to the total weight of the cosmetic agent. The total quantity of the oil component(s) is from about 0.1 to about 5.0 wt. %, relative to the total weight of the cosmetic agent. The total quantity of emulsifiers in the cosmetic agent is from about 1.5 to about 8.0 wt. %, relative to the total weight of the cosmetic agent and the weight ratio of the non-ionic emulsifier a) to the non-ionic emulsifier b) is from about 1.2:1 to about 4.0:1. The total quantity of the non-ionic emulsifier a) is from about 1.0 to about 5.0 wt. % and the total quantity of the non-ionic emulsifier b) is from about 0.5 to about 3.0 wt. %, relative to the total weight of the cosmetic agent.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

In particular, the present disclosure relates to the following points:

A cosmetic agent in the form of an O/W emulsion, containing in an aqueous cosmetically compatible carrier:
  a) at least one non-ionic emulsifier, including an ethoxylated, saturated, branched $C_{14}$-$C_{18}$ alcohol has an ethoxylation degree of from about 18 to about 22 ethylene oxide units,
  b) at least one further non-ionic emulsifier, including an ethoxylated, linear, mono-unsaturated $C_{16}$-$C_{20}$ alcohol has an ethoxylation degree of from about 18 to about 22 ethylene oxide units,
  c) at least one antiperspirant and/or deodorizing active ingredient, and
  d) at least one oil component, wherein the total quantity of emulsifiers in the cosmetic agent of is from about 1.5 to about 8.0 wt. %, relative to the total weight of the cosmetic agent, and
  the weight ratio of the non-ionic emulsifier a) to the non-ionic emulsifier b) is from about 1.2:1 to about 4.0:1.

Cosmetic agent according to point 1, exemplified in that the total quantity of the non-ionic emulsifier a) is from about 1.0 to about 5.0 wt. %, preferably from about 2.0 to about 3.0 wt. %, and the total quantity of the non-ionic emulsifier b) is from about 0.5 to about 3.0 wt. %, preferably from about 0.8 to about 1.5 wt. %, relative to the total weight of the cosmetic agent.

Cosmetic agent according to point 1 or 2, exemplified in that is contains at least one further non-ionic emulsifier, which is selected from hydrated castor oils with from about 20 mol to about 60 of ethylene oxide per mol of hydrated castor oil, preferably hydrated castor oil with around about 40 mol of ethylene oxide per mol of hydrated castor oil (INCI: PEG-40 Hydrogenated Castor Oil).

Cosmetic agent according to one of the points above, exemplified in that it contains at least one further non-ionic emulsifier, which is selected from esters of isostearic acid with 1,2-propylene glycol, preferably propylenglycolmonoisostearate.

Cosmetic agent according to one of the points above, exemplified in that the weight ratio of the non-ionic emulsifier a) to the non-ionic emulsifier b) is from about 1.2:1 to about 3.5:1, preferably from about 1.5:1 to about 2.5:1.

Cosmetic agent according to one of the points above, exemplified in that it contains about 0.1 wt. % or less of ionic surfactants.

Cosmetic agent according to one of the points above, exemplified in that the nonionic emulsifier a) is polyoxyethylene (20) isocetyl ether (INCI: isoceteth-20) and the nonionic emulsifier b) is polyoxyethylene (20) oleyl ether (INCI: oleth-20).

Cosmetic agent according to one of the aforementioned items, exemplified in that it contains no anionic surfactants.

Cosmetic agent according to one of the points above, exemplified in that it contains about 0.1 wt. % or less of cationic surfactants.

Cosmetic agent according to one of the points above, exemplified in that it contains at least one polyethylene glycol ether of the general formula R—O—(—CH$_2$—CH$_2$—O—)$_n$—R', wherein R and R' independently denote branched or unbranched alkyl, aryl or alkenyl radicals and n is an integer greater than about 75, preferably an integer from about 100 to about 400, and particularly preferably an integer from about 120 to about 200, preferably PEG-150 Distearate and/or PEG-150 Dioleate; and/or
  at least one non-ionic polyurethane polymer, which comprises at least one polyurethane unit of the formula (Ib) and/or the formula (Ic), at least one nonionic polyether unit of the formula (IIa) and at least one ether unit of the formula (IIIb),

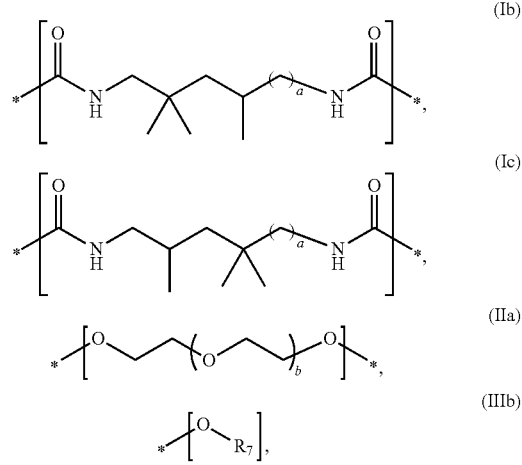

wherein
a denotes the integer 2,
b denotes integers from about 80 to about 110, and
$R_7$ denotes a branched $C_{16}$-$C_{20}$ alkyl group.

Cosmetic agent according to one of the points above, exemplified in that it contains the at least one antiperspirant active ingredient in a total quantity of from about 2.0 to about 40 wt. %, preferably from about 5.0 to about 30 wt. %, more preferably from about 10 to about 25 wt. %, and particularly preferably from about 12 to about 20 wt. %, relative to the total weight of the cosmetic agent.

Cosmetic agent according to one of the points above, exemplified in that it contains the at least one deodorizing active ingredient in a total quantity of from about 0.0001 to about 40 wt. %, preferably from about 0.2 to about 20 wt. %, more preferably from about 1.0 to about 15 wt. %, and most preferably from about 1.5 to about 5.0 wt. %, relative to the total weight of the cosmetic agent.

Cosmetic agent according to one of the points above, exemplified in that it contains, as the oil component, an ester of linear or branched, saturated or unsaturated fatty alcohols with from about 2 to about 30 carbon atoms with linear or branched, saturated or unsaturated fatty acids with from about 2 to about 30 carbon atoms, which can be hydroxylated, in particular isopropylisostearate.

Cosmetic agent according to one of the points above, exemplified in that the total quantity of the oil component(s) is from about 0.1 to about 5.0 wt. %, preferably from about 0.3 to about 4.0 wt. %, more preferably from about 0.5 to about 3.0 wt. %, and particularly preferably from about 0.6 to about 1.5 wt. %, relative to the total weight of the cosmetic agent.

Cosmetic agent according to one of the points above, exemplified in that the agent is provided in the form of an O/W emulsion with a volume average droplet size of from about 50 to about 1000 nm, preferably from about 100 to about 500 nm, more preferably from about 150 to about 400 nm, and most preferably from about 200 to about 300 nm.

Cosmetic agent according to one of the points above, exemplified in that the agent has a measured turbidity according to DIN EN ISO 7027 (C2) 2016-11 at 22° C. of from about 0 to about 150 NTU, preferably to about 80 NTU, more preferably to about 60 NTU, and particularly preferably to about 40 NTU.

Cosmetic agent according to one of the points above, exemplified in that it has a measured transmission of about 92% or more at about 22° C. and with a wavelength of about 500 nm.

Cosmetic agent according to one of the points above, exemplified in that the agent has a viscosity of from about 1200 to about 2500 cps (20° C., Brookfield, Spindle 3, 20 rpm).

Non-therapeutic cosmetic method for reducing the perspiration of the body and/or for reducing the body odor released by perspiration, wherein the cosmetic agent according to one of the points 1 to 18 is applied to the human skin and remains on the application point for at least about 1 hour.

As contemplated herein, the term "emulsifiers" should be understood as compounds that can reduce the interface tension between the different phases of the cosmetic agents and, in this manner, lead to a stabilization of the cosmetic agents. Such emulsifiers have an amphiphilic molecular structure, i.e. they have both polar and apolar groups. The polar groups are groups that have a hydrophilic character. Apolar groups are understood as hydrophobic and lipophilic groups. These emulsifiers can therefore interact with both hydrophilic and lipophilic phases. Consequently, an orientation of the emulsifiers occurs at the boundary surface between the hydrophilic and hydrophobic phase, whereby stabilization is achieved. Surfactants and "emulsifiers" form adsorption layers on the top and boundary surfaces or can aggregate in volume phases to form micelle colloids or lyotropic mesophases. Besides the oriented absorption at boundary surfaces, basic properties of the surfactants and emulsifiers are the aggregation to micelles and the formation of lyotropic phases.

The term "HLB value" also used in this description is understood as a measure introduced by Griffin in 1950 for the water or oil solubility of predominantly non-ionic surfactants. The HLB value can be determined experimentally by using, for example, the phenol titration method, in which the emulsifier solution is mixed with about a 5% phenol solution until it becomes cloudy. Furthermore, the HLB value can also be determined (gas) chromatographically by determining the permittivity or colorimetrically. The HLB value of an emulsifier mixture can be additively calculated using the values of its constituents. The scale of HLB values generally ranges from about 1 to about 20. Substances with a low HLB value of below about 8 are generally good water-in-oil emulsifiers, while hydrophilic compounds with an HLB value of about 8 and above act as oil-in-water-emulsifiers.

As contemplated herein, the term "antiperspirant active ingredient" should be understood as active ingredient that lead to a prevention or reduction of the perspiration of the sweat glands of the body.

Furthermore, as contemplated herein, the term "deodorizing active ingredient" should be understood as active ingredients that lead to a reduction or prevention of the bacterial decomposition of the sweat and/or absorb or cover the malodorous volatile decomposition products.

Finally, the total quantity of emulsifiers is understood as the total amount of all emulsifiers contained in the cosmetic agent.

Unless otherwise specified, the wt. % presently relates to the total weight of the cosmetic agents, wherein the sum of all ingredients of the agents amounts to 100 wt. %.

The cosmetic agents as contemplated herein contain the at least one non-ionic emulsifier a), the at least one further non-ionic emulsifier b), the at least one antiperspirant and/or deodorizing active ingredient c) and the at least one oil component d), and, optionally, additional ingredients in a cosmetically compatible carrier.

Preferred cosmetically compatible carriers are aqueous, alcoholic or aqueous-alcoholic media preferably having at least about 10 wt. % water, relative to the total weight of the cosmetic agent. It is particularly preferable that the cosmetically acceptable carrier contains water, particularly in a quantity that is preferably at least about 10 wt. %, more preferably at least about 20 wt. %, most preferably at least about 40 wt. % water relative to the total weight of the cosmetic agent. Particularly preferred cosmetic agents have a proportion of water of from about 50 to about 95 wt. %, preferably from about 60 to about 90 wt. % and particularly from about 65 to about 85 wt. %, relative to their total weight.

Low alcohols having from about 1 to about 4 carbon atoms are normally used for cosmetic purpose, such as ethanol and isopropanol, can be used, in particular as alcohols. Examples of water-soluble solvents as a cosolvent are glycerol and/or ethylene glycol and/or 1,2-propylene glycol, which can each be used in a quantity of from 0 to about 5.0 wt. % relative to the total weight of the cosmetic agent.

As contemplated herein, at least one nonionic emulsifier is contained as the first emulsifier a), wherein it is an ethoxylated, saturated, branched $C_{14}$-$C_{18}$ alcohol with an ethoxylation degree of from about 18 to about 22, preferably about 20, ethylene oxide units, or mixtures of two or more of these. Furthermore, the first emulsifier a) preferably has an HLB value of from about 10 to about 17, particularly preferably from about 14 to about 16.

As contemplated herein, the first emulsifier a) is preferably an ethoxylated, saturated, branched $C_{16}$ alcohol with an ethoxylation degree of from about 20 mol of ethylene oxide per mol of alcohol, or a mixture of these.

The compounds known under the INCI designations isosteareth-20 (HLB value=15; CAS No.: 52292-17-8) and isoceteth-20 (HLB value=15.7; CAS No.: 69364-63-2 and 9004-95-9) are preferred examples of ethoxylated branched $C_{14}$-$C_{18}$ alcohols with from about 18 to about 22 mol of ethylene oxide per mol of alcohol that can be used as contemplated herein. Of these, isoceteth-20 is particularly preferable as contemplated herein.

The cosmetic agent as contemplated herein contains the at least one ethoxylated, saturated, branched $C_{14}$-$C_{18}$ alcohol with an ethoxylation degree of from about 18 to about 22 (emulsifier a)), preferably in a total quantity of from about 1.0 to about 5.0 wt. %, more preferably from about 1.5 to about 4.0 wt. %, and particularly preferably from about 2.0 to about 3.0 wt. %.

As a further essential constituent, the cosmetic composition contains at least one further non-ionic emulsifier b), wherein an ethoxylated, linear, mono-unsaturated $C_{16}$-$C_{20}$ alcohol has an ethoxylation degree of from about 18 to about 22 ethylene oxide units. Furthermore, the second emulsifier b) preferably has an HLB value of from about 10 to about 17, particularly preferably from about 14 to about 16.

As contemplated herein, the second emulsifier b) is preferably an ethoxylated, linear, mono-unsaturated $C_{16}$ alcohol with an ethoxylation degree of about 20 mol of ethylene oxide per mol of alcohol. A particularly preferred second nonionic emulsifier b) is oleth-20 (HLB value=15.3; CAS No.: 9004-98-2).

The cosmetic agent as contemplated herein contains the at least one non-ionic emulsifier b), wherein an ethoxylated, linear, mono-unsaturated $C_{16}$-$C_{20}$ alcohol has an ethoxylation degree of from about 18 to about 22 ethylene oxide units, preferably in a total quantity of from about 0.5 to about 3.5 wt. %, more preferably from about 0.7 to about 3.0 wt. %, and particularly preferably from about 0.8 to about 1.5 wt. %.

To obtain the effect of improved stability even under temperature fluctuations, it is necessary, as contemplated herein, that the cosmetic agent contains the emulsifier a) and the emulsifier b) in a weight ratio of from about 1.2:1 to about 4.0:1, preferably from about 1.5:1 to about 3.5:1, likewise preferably from about 1.5:1 to about 2.5:1 specified as total quantity of emulsifier a):total quantity of emulsifier b)).

In addition to the specified non-ionic emulsifiers, other emulsifiers can be contained in the cosmetic agent as contemplated herein. This can include other nonionic emulsifiers and, in small quantities, also ionic surfactants, i.e. cationic, anionic and/or zwitterionic or amphoteric surfactants. Ionic surfactants are preferably contained in the present disclosure, but only in a total quantity of about 0.2 wt. % or less, more preferably about 0.1 wt. % or less. Cationic surfactants up to about 0.1 wt. % can be contained in embodiments of the present disclosure. Anionic surfactants are particularly preferably not contained in the cosmetic agent as contemplated herein, i.e. preferably in a total quantity of 0 wt. %.

Further nonionic emulsifiers that can be contained are preferably those with an HLB value of from about 10 to about 17 that do not fall under the definitions of emulsifier a) and emulsifier b). These are selected, for example, from the group of mono- and/or di- and/or triglycerides of coconut oil with about 7 mol of ethylene oxide per mol of glyceride, mono- and/or diglycerides of almond oil with from about 20 to about 60 mol of ethylene oxide per mol of glyceride, hydrated castor oil with from about 25 mol to about 60 mol of ethylene oxide per mol of hydrated castor oil, N-(2-hydroxyethyl)octadecanamide, mono- and/or tri-sorbitan oleates with from about 20 mol of ethylene oxide per mol of sorbitan, mono-sorbitan stearates and/or mono-sorbitan laurates with about 20 mol of ethylene oxide per mol of sorbitan, ethoxylated fatty acids from olive oil with about 7 mol of ethylene oxide per mol of fatty acid, $C_{16}$-$C_{18}$ alkyl glucosides, esters of oleic acid and/or lauric acid with about 8 mol of ethylene oxide per mol of acid, polymers of methyl-D-glucopyranoside dioctadecanoate with glycerol, N-(2-hydroxyethyl)dodecanamide, methyl-β-D-glucoside sesquistearates with about 20 mol of ethylene oxide per mol of glucose ester. The mono- and/or di- and/or triglycerides of coconut oil with about 7 mol of ethylene oxide per mol of glyceride used in the context of the present disclosure is, for example, the compound known under the INCI designation PEG-7 Glyceryl Cocoate (HLB value=10; CAS No.: 68201-46-7). Additional emulsifiers used in the context of the present disclosure in the form of mono- and/or diglycerides of almond oil with from about 20 to about 60 mol of ethylene oxide per mol of glyceride, preferably with an HLB value of from about 10 to about 17, are, for example, the compounds known under the INCI designations PEG-20 Almond Glycerides (HLB value=10; CAS No.: 124046-50-0) and PEG-60 Almond Glycerides (HLB value=15; CAS No.: 226993-90-4). Other suitable additional emulsifiers are hydrated castor oil with about 25 mol of ethylene oxide per mol of hydrated castor oil, which is known under the INCI designation PEG-25 Hydrogenated Castor Oil (HLB value=10.8; CAS No.: 61788-85-0), or preferably hydrated castor oil with about 40 mol of ethylene oxide per mol of hydrated castor oil with the INCI designation PEG-40 Hydrogenated Castor Oil (HLB value=14-16). Additional mono- and/or tri-sorbitan oleates with about 20 mol of ethylene oxide per mol of sorbitan used as contemplated herein include, for example, the compounds known under the INCI designations polysorbate 80 (HLB value=15; CAS No.: 9005-65-6) and polysorbate 85 (HLB value=11; CAS No.: 9005-70-3). Furthermore, mono-sorbitan stearates and/or mono-sorbitan laurates with 20 mol of ethylene oxide per mol of sorbitan, preferably with an HLB value of from about 10 to about 17, which, for example, are known under the INCI designations polysorbate 60 (HLB value=14.9; CAS No.: 9005-67-8) and polysorbate 20 (HLB value=16.7; CAS No.: 9005-64-5), are also suitable as additional emulsifiers. The compounds known under the INCI designations oleth-10 (HLB value=12.4; CAS No.: 9004-98-2), ceteth-10 (HLB value=12.9; CAS No.: 9004-95-9), ceteareth-20 (HLB value=15.2; CAS No.: 68439-49-6), steareth-20 (HLB value=15.3; CAS No.: 9005-00-9), steareth-21 (HLB value=15.5; CAS No.: 9005-00-9), ceteth-20 (HLB value=15.7; CAS No.: 9004-95-9) and Laureth-23 (HLB value=16.9; CAS No. 9002-92-0) are examples of additional ethoxylated linear $C_{10}$-$C_{22}$ alcohols with from about 10 to about 23 mol of ethylene oxide per mol of alcohol used as contemplated herein, which are not included among the emulsifiers a) and b). Ethoxylated fatty acids from olive oil with about 7 mol of ethylene oxide per mol of fatty acid and $C_{16}$-$C_{18}$ alkyl glucoside, preferably with an HLB value of from about 10 to about 17, which, for example, are known under the INCI designations PEG-7 Olivate (HLB value=11; CAS No.: 226708-41-4) and cetearyl glucoside (HLB value=11; CAS No.: 54549-27-8 (C16), 27836-65-3 (C18)), are also suitable as additional emulsifiers. Furthermore, esters of oleic acid and/or lauric acid with an average of about 8 mol of ethylene oxide per mol of acid and polymers of methyl-D-glucopyranoside dioctadecanoate with glycerol, which, for example, are known under the INCI designations PEG-8 Oleate (HLB value=11.6; CAS No.: 9004-96-0), PEG-8 Laurate (HLB value=13; CAS No.: 9004-81-3) and polyglyceryl-3 methylglucose distearate (HLB value=12; CAS No.: 68986-95-8), can be used as contemplated herein. Finally, methyl β-D-glucoside sesquistearates with about 20 mol of ethylene oxide per mol of glucose ester, which, for example, are known under the INCI designation PEG-20 Methyl Glucose Sesquistearate (HLB value=15; CAS No.: 68389-70-8), are also used as contemplated herein. The total weight of these optional additionally contained emulsifiers is preferably zero to about 2 wt. %, more preferably from about 0.1 to about 1.5 wt. %, particularly preferably from about 0.5 to about 1 wt. %, relative to the total weight of the cosmetic agents as contemplated herein.

At least one nonionic emulsifier with an HLB value of from about 1 to about 6 can also be contained in preferred embodiments of the present disclosure. Preferred cosmetic agents as contemplated herein are exemplified in that the at least one emulsifier with an HLB value of from about 1 to about 6 is selected from the group of mono- and/or diesters of sorbitan with oleic acid, stearic acid or isostearic acid, esters of isostearic acid with propylene oxide, lecithins, ethoxylated $C_{12}$-$C_{20}$ alcohols with about 2 mol of alcohol per mol of ethylene oxide, and in particular esters of isostearic acid with 1,2-propylene glycol.

A particularly preferable ester of isostearic acid with 1,2-propylene glycol used as contemplated herein is, for example, the compound known under the INCI designation propylene glycol isostearate (HLB value=2.5; CAS No.: 63799-53-1).

The at least one emulsifier with an HLB value of from about 1 to about 6, preferably the esters of isostearic acid with 1,2-propylene glycol, in particular 2-hydroxypropyl-16-methyl heptadecanoate (INCI: propylene glycol monoisostearate), is preferably contained in specific quantity ranges. Preferred cosmetic agent as contemplated herein are therefore exemplified in that the at least one emulsifier with an HLB value from about 1 to about 6 is contained in a total amount of from about 0.1 to about 1.7 wt. %, preferably from about 0.2 to about 1.5 wt. %, more preferably from about 0.3 to about 1.2 wt. %, particularly preferably from about 0.4 to about 1.0 wt. %, relative to the total weight of the cosmetic agent. The aforementioned quantities relate to the total quantity of emulsifiers with an HLB value of from about 1 to about 6. Consequently, if about 2 or more emulsifiers with an HLB value of from about 1 to about 6 are used, the aforementioned quantities relate to their total quantity.

In the cosmetic agents as contemplated herein, the weight ratio of the sum of the emulsifiers a) and b) to the emulsifier with an HLB value of from about 1 to about 6 is preferably from about 10:1 to about 2:1, more preferably from about 8:1 to about 3:1. The use of the weight ratios listed above can contribute to an improvement in stability under temperature fluctuations.

As contemplated herein, the total quantity of emulsifiers in the cosmetic agent is from about 1.5 to about 8.0 wt. %, more preferably from about 2.0 to about 7.0 wt. %, and particularly preferably from about 3.0 to about 6.0 wt. %. Due the low emulsifier concentration, the cosmetic agents as contemplated herein have a high skin tolerance and excellent cosmetic properties.

Furthermore, thickening or crosslinking substances can be contained in order to adjust the viscosity of the cosmetic agent to the desired ranges for the respective application. As contemplated herein, the thickening or crosslinking substances used are preferably also designated as associative thickeners, preferably highly ethoxylated compounds with two or more long-chain alkyl substituents.

This preferably includes cross-linkers from the group of
polyethylene glycol ethers of the general formula R—O—(—CH$_2$—CH$_2$—O—)$_n$—R', wherein R and R' independently denote branched or unbranched alkyl, aryl or alkenyl radicals and n is an integer greater than about 75, preferably an integer from about 100 to about 400, and particularly preferably an integer from about 120 to about 200, for example PEG-150 Distearate and/or PEG-150 Dioleate, etherified fatty acid ethoxylates of the general formula R—COO—(—CH$_2$—CH$_2$—O—)$_n$—R', wherein R and R' independently denote branched or unbranched alkyl, aryl or alkenyl radicals and n is an integer greater than about 75, preferably an integer from about 100 to about 400, and particularly preferably an integer from about 120 to about 200, esterified fatty acid ethoxylates of the general formula R—COO—(—CH$_2$—CH$_2$—O—)—C(O)—R', wherein R and R' independently denote branched or unbranched alkyl, aryl or alkenyl radicals and n is an integer greater than about 75, preferably an integer from about 100 to about 400, and particularly preferably an integer from about 120 to about 200, polypropylene glycol ethers of the general formula R—O—(—CH$_2$—CH(CH$_3$)—O—)$_n$—R', wherein R and R' independently denote branched or unbranched alkyl, aryl or alkenyl radicals and n is an integer greater than about 75, preferably an integer from about 100 to about 400, and particularly preferably an integer from about 120 to about 200, esterified fatty acid propoxylates of the general formula R—COO—(—CH$_2$—CH(CH$_3$)—O—)$_n$—C(O)—R', wherein R and R' independently denote branched or unbranched alkyl, aryl or alkenyl radicals and n is an integer greater than about 75, preferably an integer from about 100 to about 400, and particularly preferably an integer from about 120 to about 200, polypropylene glycol ethers of the general formula R—O—X$_n$—Y$_m$—R', wherein R and R' denote branched or unbranched alkyl, aryl or alkenyl radicals, wherein X and Y are not identical and each denote either an oxyethylene group or an oxypropylene group, and n and m independently denote integers, the sum of which is greater than about 75, preferably an integer from about 100 to about 400, and particularly preferably an integer from about 120 to about 200 and etherified fatty acid propoxylates of the general formula R—COO—X$_n$—Y$_m$—R', wherein R and R' denote branched or unbranched alkyl, aryl or alkenyl radicals, wherein X and Y are not identical and each denote either an oxyethylene group or an oxypropylene group, and n and m independently denote integers, the sum of which is greater than about 75, preferably an integer from about 100 to about 400, and particularly preferably an integer from about 120 to about 200.

Among these, particular preference is given to polyalkylene glycol ethers of the general formula R—O—(CH$_2$—CH$_2$—O)$_n$—R' or R—O—(CH$_2$—CH(CH$_3$)—O)$_n$—R' and polyalkylene glycol esters of the general formula R—COO—(CH$_2$—CH$_2$—O)$_n$—C(O)—R' or R—COO—(CH$_2$—CH(CH$_3$)—O)$_n$—C(O)—R', wherein R and R' independently denote a linear or branched C$_6$-C$_{30}$ alkyl or C$_6$-C$_{30}$ alkenyl group, and n, the number of alkylenoxide units, denotes an integer greater than about 75, preferably an integer from about 100 to about 400, and particularly preferably an integer from about 120 to about 200. R and R' are preferably independently a decyl, undecyl, lauryl, tridecyl, tetradecyl, pentadecyl, hexadecyl, heptadecyl, heptadecenyl, octadecyl, octadecenyl, stearyl, oleyl, nonadecyl, nonadecenyl, eicosyl, eicosenyl, docosyl, docosenyl or behenyl group.

As contemplated herein, the polyethylene glycol ethers and polyethylene glycol esters are particularly preferable, in particular PEG-150 Distearate, PEG-150 Dioleate, PEG-120 Methyl Glucose Dioleate, PEG-300 Pentaerythrityl Tetraisostearate, PEG-350 Sorbitan Isostearate and PEG-230 Glyceryl Isostearate.

As a further, thickener, preferably at least one nonionic polyurethane polymer can be alternatively or additionally contained, comprising at least one polyurethane unit of the formula (Ib) and/or the formula (Ic), at least one nonionic polyether unit of the formula (IIa) and at least one ether unit of the formula (IIIb)

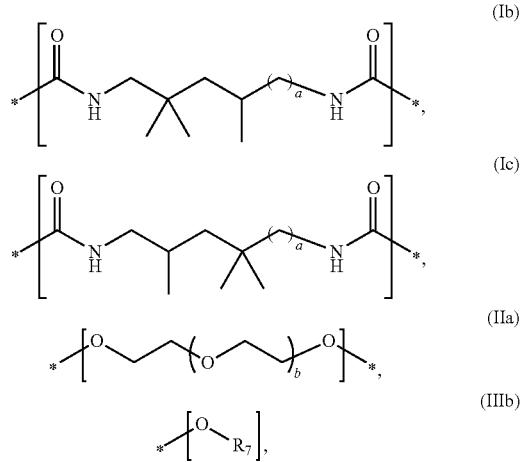

wherein
a denotes the integer 2,
b denotes integers from about 80 to about 110, and
R$_7$ denotes a branched C$_{16}$-C$_{20}$ alkyl group, The use of such nonionic polyurethane polymers in the cosmetic agents as contemplated herein permits a low total emulsifier concentration and can contribute to good storage stability under temperature fluctuations and good cosmetic properties. Due to the low total emulsifier concentration, these agents have excellent skin tolerances. In particular, the use of these polyurethane polymers leads to a thickening of preferred cosmetic agents, meaning that no further thickeners are contained in preferred embodiments of the present disclosure.

The use of non-ionic polyurethane polymers, which contain polyurethane units of the formulae (Ib) and/or (Ic), nonionic polyether units of the formula (IIa) and ether units of the formula (IIIb), and/or the aforementioned polyethylene glycol ethers of the general formula R—O—(—CH$_2$—CH$_2$—O—)$_n$—R', leads to a thickening of the emulsion, meaning that favorable viscosities can be achieved for roll-on-application. As contemplated herein, it is particularly preferred that the at least one nonionic polyurethane polymer is a copolymer of trimethylhexane diisocyanate (TMHDI) and polyethylene glycol with an average of about 90 ethylene oxide units, terminally modified with a branched C$_{16}$-C$_{20}$ alcohol. For example, this is commercially available as Rheoluxe® 880 (Elementis), an approx. 30 wt. % solution/dispersion of Bis-C$_{16}$-C$_{20}$ isoalkoxy TMHDI/PEG-90 Copolymer in 1,2-propylene glycol (approx. 55 wt.-%) and water (approx. 15 wt.-%). Such nonionic polyurethane polymers have hydrophobic end groups in the form of branched C$_{16}$-C$_{20}$ alkyl groups and a hydrophilic middle part due to the use of polyethylene glycol. Consequently, such polyurethanes are also capable of effectively stabilizing and crosslinking micelles formed in the cosmetic agents.

The thickening agents or cross-linkers are preferably used in specific quantity ranges. As contemplated herein, it is preferred that the at least one thickener is contained in a total quantity of from about 0.2 to about 4.0 wt. %, preferably from about 0.5 to about 3.0 wt. %, more preferably from about 0.6 to about 2.0 wt. %, particularly preferably from about 0.7 to about 1.5 wt. %, and most preferably from about 0.8 to about 1.2 wt. %, relative to the total weight of the cosmetic agent. This leads to excellent stabilization of the preferred cosmetic agents as contemplated herein, without incompatibilities with other ingredients occurring. In particular, only the non-ionic polyurethane polymers described above, which contain at least one polyurethane unit of the formula (Ib) and/or (Ic), at least one non-ionic Polyether unit of the formula (IIa) and at least one ether unit of the formula (IIIb), and/or the aforementioned polyethylene glycol ethers of the general formula R—O—(—CH$_2$—CH$_2$—O—)$_n$—R', are preferably used as the thickener.

As a further essential constituent c), the cosmetic agent as contemplated herein contains at least one antiperspirant and/or deodorizing active ingredient.

Aluminum salts and/or aluminum zirconium salts are preferably used as antiperspirant active ingredients in the context of the present disclosure. Cosmetic agents as contemplated herein are therefore exemplified in that the at least one antiperspirant active ingredient is selected from the group of (i) water-soluble astringent inorganic salts of aluminum, in particular aluminum chlorohydrate, aluminum sesquichlorohydrate, aluminum dichlorohydrate, aluminum hydroxide, potassium aluminum sulphate, aluminum bromohydrate, aluminum chloride, aluminum sulphate; (ii) water-soluble astringent organic salts of aluminum, in particular aluminum chlorhydrex-propylene glycol, aluminum chlorhydrex-polyethylene glycol, aluminum-propylene glycol complexes, aluminum sesquichlorohydrex-propylene glycol, aluminum sesquichlorohydrex-polyethylene glycol, aluminum-propylene glycol-dichlorohydrex, aluminum-polyethylene glycol-dichlorohydrex, sodium aluminum lactate, sodium aluminum hydroxy lactate, aluminum lipo amino acids, aluminum lactate, aluminum chlorohydroxyallantoinate, sodium aluminum chlorohydroxy lactate; (iii) water-soluble astringent inorganic aluminum zirconium salts, in particular aluminum zirconium trichlorohydrate, aluminum zirconium tetrachlorohydrate, aluminum zirconium pentachlorohydrate, aluminum zirconium octachlorohydrate; (iv) water-soluble astringent organic aluminum zirconium salts, in particular aluminum zirconium propylene glycol complexes, aluminum zirconium trichlorohydrex glycine, aluminum zirconium tetrachlorohydrex glycine, aluminum zirconium pentachlorohydrex glycine, aluminum zirconium octachlorohydrex glycine; and (v) mixtures thereof.

As contemplated herein, the expression "antiperspirant aluminum salts" does not include aluminosilicates or zeolithes. Moreover, as contemplated herein, water-soluble aluminum salts are those salts which have a solubility of at least from about 3 wt. % at about 20° C., i.e. at least about 3 g of the antiperspirant aluminum salt dissolve in about 97 g of water at about 20° C.

Particularly preferred inorganic aluminum salts are selected from aluminum chlorohydrate, particularly aluminum chlorohydrate with the general formula $[Al_2(OH)_5 Cl.1\text{-}6\ H_2O]_n$, preferably $[Al_2(OH)_5Cl.2\text{-}3\ H_2O]_n$, which can be in non-activated (polymerized) or in activated form (depolymerized), as well as aluminum chlorohydrate with the general formula $[Al_2(OH)_4Cl_2.1\text{-}6\ H_2O]_n$, preferably $[Al_2(OH)_4Cl_2.2\text{-}3\ H_2O]_n$, which can be in non-activated (polymerized) or in activated form (depolymerized). The production of such antiperspirant aluminum salts is disclosed, for example, in the publications U.S. Pat. Nos. 3,887,692 A, 3,904,741 A, 4,359,456 A, GB 2 048 229 A and GB 1 347 950 A.

As contemplated herein, particularly preferred antiperspirant aluminum salts are selected from so-called "activated" aluminum salts, which are also designated as antiperspirant active ingredients "with enhanced activity". Such active ingredients are known from the prior art and are also commercially available. Their production is disclosed, for example, in the publications GB 2 048 229 A, U.S. Pat. Nos. 4,775,528 A and 6,010,688 A. Activated aluminum salts typically have an HPLC-peak 4-to-peak 3 surface ratio of at least about 0.4, preferably of at least about 0.7, particularly of at least about 0.9, wherein at least about 70% of the aluminum are associated with these HPLC-peaks.

In this context, "activated" aluminum zirconium salts are also known, which have a high HPLC-peak 5-aluminum content, particularly about a peak 5 surface of at least about 33%, preferably of at least about 45%, relative to the total surface under peaks from about 2 to about 5 measured with HPLC of about a 10 wt. % aqueous solution of the active ingredient under conditions in which the aluminum species are dissolved in at least about 4 peaks in succession (identified as peaks from about 2 to about 5). Preferred aluminum-zirconium salts with a high HPLC-peak 5-aluminum content (also designated as "$E^5AZCH$") are, for example, disclosed in the publications U.S. Pat. Nos. 6,436,381 A and 6,649,152 A. The aforementioned activated aluminum zirconium salt can also be stabilized with a water-soluble strontium salt and/or with a water-soluble calcium salt, as is disclosed in U.S. Pat. No. 6,923,952 A, for example.

In the context of the present disclosure, basic calcium aluminum salts can be used as antiperspirant aluminum salts, as disclosed, for example, in the publication U.S. Pat. No. 2,571,030 A. These salts can be obtained by reacting calcium carbonate with aluminum chlorohydroxide or aluminum chloride and aluminum powder or by adding calcium chloride dihydrate to aluminum chlorohydroxide. It is also possible to use aluminum zirconium complexes, which are buffered with salts of amino acids, in particular with alkali and alkaline earth glycinates, and as disclosed, for example, in the publication U.S. Pat. No. 4,017,599 A.

As contemplated herein, particularly preferred antiperspirant aluminum salts have a molar metal-to-chloride ratio of from about 1.9 to about 2.1. The metal-to-chloride ratio of particularly preferred aluminum sesquichlorohydrates in the context of the present disclosure is from about 1.5:1 to about 1.8:1. Preferred aluminum zirconium tetrachlorohydrates have a molar ratio of Al:Zr of from about 2 to 6 and of metal:chloride of from about 0.9 to about 1.3, wherein particular preference is given to salts with a molar metal-to-chloride ratio of from about 0.9 to about 1.1, preferably from about 0.9 to about 1.0.

The antiperspirant active ingredient, in particular at least one aforementioned aluminum salt and/or aluminum zirconium salt, is preferably used in specific quantity ranges. Preferred cosmetic agents as contemplated herein are therefore exemplified in that the at least one antiperspirant active ingredient is contained in a total quantity of from about 2.0 to about 40 wt. %, preferably from about 3.0 to about 35 wt. %, more preferably from about 4.0 to about 32 wt. %, even more preferably from about 5.0 to about 30 wt. %, particularly preferably from about 8.0 to about 25 wt. %, and most preferably from about 10 to about 20 wt. %, relative to the total weight of the cosmetic agent. The use of the aforementioned quantities of the at least one antiperspirant active ingredient ensures an adequate antiperspirant effect and does not result in skin intolerances or negative interactions with other ingredients of the agent as contemplated herein.

In addition to and/or instead of the aforementioned antiperspirant active ingredient, the cosmetic agent can contain at least one deodorizing active ingredient.

In the context of the present disclosure, it is preferred that the at least one deodorizing active ingredient is selected from the group of (i) silver salts; (ii) aromatic alcohols, in particular 2-benzylheptan-1-ol and mixtures of 2-benzylheptan-1-ol and phenoxyethanol; (iii) 1,2-alkanediols having from about 5 to about 12 carbon atoms, in particular 3-(2-ethylhexyloxy)-1,2-propanediol; (iv) triethyl citrates; (v) active ingredients against exoesterases, in particular against arylsulfatase, lipase, beta-glucuronidase and cystathionine β-lyase; (vi) cationic phospholipids; (vii) odor absorbers, in particular silicates, such as montmorillonite, kaolinite, illite, beidellite, nontronite, saponite, hectorite, bentonite, smectite and talcum, zeolites, zinc ricinoleate, cyclodextrins; (viii) deodorizing ion exchangers; (ix) germ-inhibiting agents; (x) prebiotically effective components; and (xi) mixtures thereof.

Preferably, the deodorizing active ingredient is used in specific quantity ranges. Preferred cosmetic agents as contemplated herein are therefore exemplified in that the at least one deodorizing active ingredient is contained in a total amount of from about 0.0001 to about 40 wt. %, preferably from about 0.2 to about 20 wt. %, more preferably from about 1.0 to about 15 wt. %, and particularly preferably from about 1.5 to about 5.0 wt. %, relative to the total weight of the cosmetic agent. The use of the aforementioned quantities of the at least one deodorizing active ingredient ensures an adequate deodorizing effect and does not result in negative interactions with other ingredients of the agent as contemplated herein.

The cosmetic agents as contemplated herein in the form of O/W emulsions contain as an essential component d) at least one oil component as the oil phase, which contains at least one compound selected from the group of (i) volatile non-silicone oils, in particular liquid paraffin oils and isoparaffin oils, such as isodecane, isoundecane, isododecane, isotridecane, isotetradecane, isopentadecane, isohexadecane and isoeicosane; (ii) non-volatile non-silicone oils, in particular the esters of linear or branched, saturated or unsaturated $C_{2\text{-}30}$-fatty alcohols with linear or branched, saturated or unsaturated $C_{2\text{-}30}$-fatty acids, which can be hydroxylated, the $C_8\text{-}C_{22}$-fatty alcohol esters of monohydric or polyhydric $C_2$-$C_7$-hydroxycarboxylic acids, the triethyl citrates, the branched saturated or unsaturated $C_{6-30}$-fatty alcohols, the mono-, di- and triglycerides of linear or branched, saturated or unsaturated, optionally hydroxylated $C_{8-30}$-fatty acids, the dicarboxylic acid esters of linear or branched $C_2$-$C_{10}$-alkanols, the addition products of ethylene oxide and/or propylene oxide onto mono- or multivalent $C_{3-22}$-alkanols, which may optionally be esterified, the symmetrical, asymmetric or cyclic esters of carbonic acid with fatty alcohols, the esters of dimeric unsaturated $C_{12-22}$-fatty acids with monohydric, linear, branched and cyclic $C_{2-18}$-alkanols or $C_{2-6}$-alkanols, the benzoic esters of linear or branched $C_{8-22}$-alkanols, such as the benzoic acid $C_{12-15}$-alkyl ester and the benzoic acid isostearyl ester and the benzoic acid octyldodecyl ester, the synthetic hydrocarbons, such as polyisobutene and polydecenes, the alicyclic hydrocarbons; and (iii) mixtures thereof.

Among the non-volatile non-silicone oils, esters of linear or branched, saturated or unsaturated $C_{2-30}$ fatty alcohols with linear or branched, saturated or unsaturated $C_{2-30}$ fatty acids are particularly preferred, wherein isopropylisostearate is a particularly preferred oil component. In preferred embodiments of the present disclosure, only the esters of linear or branched, saturated or unsaturated $C_{2-30}$ fatty alcohols with linear or branched, saturated or unsaturated $C_{2-30}$ fatty acids are contained as the oil component, more preferably only isopropylisostearate.

As contemplated herein, volatile non-silicone oils in the form of $C_{10-13}$ isoparaffin mixtures having a vapor pressure of from about 10 to about 400 Pa (from about 0.08 to about 3 mm Hg), preferably from about 13 to about 100 Pa (from about 0.1 to about 0.8 mm Hg), at about 20° C. and an environmental pressure of about 1.013 hPa can also be used.

The cosmetic agents as contemplated herein preferably contain at least one oil component in a total quantity of from about 0.1 to about 5.0 wt. %, preferably from about 0.3 to about 4.0 wt. %, more preferably from about 0.5 to about 3.0 wt. %, most preferably from about 1.0 to about 2.0 wt. %, relative to the total weight of the cosmetic agent.

Other typical constituents of cosmetic agents, such as perfumes and preservatives, can be contained in the cosmetic agents of the present disclosure. As contemplated herein, perfumes are not considered oil components.

Particularly preferred cosmetic agents are exemplified in that they are provided in the form of an O/W emulsion, which is as transparent as possible, with a volume average particle diameter $D_{50}$ of from about 50 to about 1000 nm, preferably from about 100 to about 500 nm, particularly preferably from about 150 to about 400 nm, and most preferably from about 200 to about 300 nm. The volume average particle diameter of the particles or droplets present in the emulsion can be determined, for example, using laser diffraction (Roland I. et. al.; *Systematic characterization of oil-in-water emulsions for formulation design"; Int. J. of Pharmaceutics,* 2003, 263, pages 85 to 94). O/W emulsions having the aforementioned particle sizes are also designated as microemulsions in the context of the present disclosure. As contemplated herein, transparent O/W emulsions are understood as emulsions that have an NTU value (Nephelometric Turbidity Unit) of zero to about 150 NTU, preferably a maximum of 80 NTU, particularly preferably a maximum of 60 NTU, and most preferably a maximum of 40 NTU, in each case measured at 22° C. The NTU value is a measurement of transparency and represents the turbidity of the emulsion measured with a calibrated nephelometer. The NTU value of the O/W emulsions as contemplated herein can be determined, for example, using a turbidimeter, as described in patent application WO2016012327 A2. At 22° C., cosmetic agents as contemplated herein have a measured turbidity according to DIN EN ISO 7027 (C2) 2016-11 of 0 to 150 NTU, preferably up to 80 NTU, more preferably up to 60 NTU, particularly preferably up to 40 NTU, and most preferably up to 30 NTU.

The cosmetic agents as contemplated herein preferably have a transmission of about 92% or more, determined at 22° C. and with a light wavelength of 500 nm. As contemplated herein, a device such as LICO 400 (long), for example, can be used to determine the transmission.

The cosmetic agents as contemplated herein preferably have a viscosity in the range of from about 1200 to about 2500 cps (20° C., Brookfield DV-II+ Pro viscometer, Spindle 3, 20 rpm). As contemplated herein, the viscosity can preferably be adjusted in particular by one or more of the aforementioned thickeners.

O/W emulsions as contemplated herein can be produced using the methods known from the prior art.

The tables below show most preferred cosmetic agents as contemplated herein, which are provided in the form of an O/W emulsion with a volume average particle diameter $D_{50}$ of preferably from about 10 to about 400 nm, more preferably about 10 to about 200 nm (all values in wt. %, unless otherwise stated):

|  | K1 | K2 | K3 | K4 |
|---|---|---|---|---|
| Emulsifier a) | 1.0 to 5.0 | 1.5 to 4.0 | 2.0 to 3.0 | 2.0 to 3.0 |
| Emulsifier b) | 0.5 to 3.5 | 0.7 to 3.0 | 0.8 to 2.0 | 0.8 to 1.5 |
| Weight ratio of emulsifier a):Emulsifier b) | 1.2:1 to 4.0:1 | 1.5:1 to 3.5:1 | 1.5:1 to 3.5:1 | 1.5:1 to 3.5:1 |
| Low-HLB emulsifier: ester of isostearic acid with propylene oxide | 0.1 to 1.7 | 0.2 to 1.5 | 0.3 to 1.2 | 0.4 to 1.0 |
| Emulsifier: hydrated castor oil with 20 to 60 EO | 0.1 to 4.0 | 0.2 to 3.0 | 0.3 to 2.0 | 0.5 to 1.5 |
| Antiperspirant active ingredient c) | 2.0 to 40 | 5.0 to 30 | 8.0 to 25 | 10 to 20 |
| Oil component d) | 0.1 to 5.0 | 0.3 to 4.0 | 0.5 to 3.0 | 0.6 to 1.5 |
| Cosmetic carrier (aqueous or aqueous-glycolic carrier) | ad 100 | ad 100 | ad 100 | ad 100 |

|  | K5 | K6 | K7 | K8 |
|---|---|---|---|---|
| Emulsifier a) | 1.0 to 5.0 | 1.5 to 4.0 | 2.0 to 3.0 | 2.0 to 3.0 |
| Emulsifier b) | 0.5 to 3.5 | 0.7 to 3.0 | 0.8 to 2.0 | 0.8 to 1.5 |
| Weight ratio of emulsifier a):Emulsifier b) | 1.2:1 to 4.0:1 | 1.5:1 to 3.5:1 | 1.5:1 to 3.5:1 | 1.5:1 to 3.5:1 |

-continued

| | | | | |
|---|---|---|---|---|
| Low-HLB emulsifier: ester of isostearic acid with propylene oxide | 0.1 to 1.7 | 0.2 to 1.5 | 0.3 to 1.2 | 0.4 to 1.0 |
| Emulsifier: hydrated castor oil with 20 to 60 EO | 0.1 to 4.0 | 0.2 to 3.0 | 0.3 to 2.0 | 0.5 to 1.5 |
| Deodorizing active ingredient c) | 0.0001 to 40 | 0.2 to 20 | 1.0 to 15 | 1.5 to 5.0 |
| Oil component d) | 0.1 to 5.0 | 0.3 to 4.0 | 0.5 to 3.0 | 0.6 to 1.5 |
| Cosmetic carrier (aqueous or aqueous-glycolic carrier) | ad 100 | ad 100 | ad 100 | ad 100 |

| | K9 | K10 | K11 | K12 |
|---|---|---|---|---|
| Emulsifier a) isoceteth-20 | 1.0 to 5.0 | 1.5 to 4.0 | 2.0 to 3.0 | 2.0 to 3.0 |
| Emulsifier b) oleth-20 | 0.5 to 3.5 | 0.7 to 3.0 | 0.8 to 2.0 | 0.8 to 1.5 |
| Weight ratio of emulsifier a):Emulsifier b) | 1.2:1 to 4.0:1 | 1.5:1 to 3.5:1 | 1.5:1 to 3.5:1 | 1.5:1 to 3.5:1 |
| Low-HLB emulsifier: propylene glycol isostearate | 0.1 to 1.7 | 0.2 to 1.5 | 0.3 to 1.2 | 0.4 to 1.0 |
| PEG-40 Hydrogenated Castor Oil | 0.1 to 4.0 | 0.2 to 3.0 | 0.3 to 2.0 | 0.5 to 1.5 |
| Antiperspirant active ingredient c): aluminum chlorohydrate and/or aluminum sesquichlorohydrate | 2.0 to 40 | 5.0 to 30 | 8.0 to 25 | 10 to 20 |
| Oil component d), preferably isopropylisostearate | 0.1 to 5.0 | 0.3 to 4.0 | 0.5 to 3.0 | 0.6 to 1.5 |
| Cosmetic carrier (aqueous or aqueous-glycolic carrier) | ad 100 | ad 100 | ad 100 | ad 100 |

| | K13 | K14 | K15 | K16 |
|---|---|---|---|---|
| Emulsifier a) isoceteth-20 | 1.0 to 5.0 | 1.5 to 4.0 | 2.0 to 3.0 | 2.0 to 3.0 |
| Emulsifier b) oleth-20 | 0.5 to 3.5 | 0.7 to 3.0 | 0.8 to 2.0 | 0.8 to 1.5 |
| Weight ratio of emulsifier a):Emulsifier b) | 1.2:1 to 4.0:1 | 1.5:1 to 3.5:1 | 1.5:1 to 3.5:1 | 1.5:1 to 3.5:1 |
| Further emulsifier: propylene glycol isostearate | 0.1 to 1.7 | 0.2 to 1.5 | 0.3 to 1.2 | 0.4 to 1.0 |
| PEG-40 Hydrogenated Castor Oil | 0.1 to 4.0 | 0.2 to 3.0 | 0.3 to 2.0 | 0.5 to 1.5 |
| Deodorizing active ingredient c) | 0.0001 to 40 | 0.2 to 20 | 1.0 to 15 | 1.5 to 5.0 |
| Oil component d), preferably isopropylisostearate | 0.1 to 5.0 | 0.3 to 4.0 | 0.5 to 3.0 | 0.6 to 1.5 |
| Cosmetic carrier (aqueous or aqueous-glycolic carrier) | ad 100 | ad 100 | ad 100 | ad 100 |

| | K17 | K18 | K19 | K20 |
|---|---|---|---|---|
| Emulsifier a) | 1.0 to 5.0 | 1.5 to 4.0 | 2.0 to 3.0 | 2.0 to 3.0 |
| Emulsifier b) | 0.5 to 3.5 | 0.7 to 3.0 | 0.8 to 2.0 | 0.8 to 1.5 |
| Weight ratio of emulsifier a):Emulsifier b) | 1.2:1 to 4.0:1 | 1.5:1 to 3.5:1 | 1.5:1 to 3.5:1 | 1.5:1 to 3.5:1 |
| Emulsifier: ester of isostearic acid with propylene oxide | 0.1 to 1.7 | 0.2 to 1.5 | 0.3 to 1.2 | 0.4 to 1.0 |
| Emulsifier: hydrated castor oil with 20 to 60 EO | 0.1 to 4.0 | 0.2 to 3.0 | 0.3 to 2.0 | 0.5 to 1.5 |
| Antiperspirant active ingredient c) | 2.0 to 40 | 5.0 to 30 | 8.0 to 25 | 10 to 20 |
| Oil component d) | 0.1 to 5.0 | 0.3 to 4.0 | 0.5 to 3.0 | 0.6 to 1.5 |
| Thickener* | 0.2 to 4.0 | 0.5 to 3.0 | 0.6 to 2.0 | 0.7 to 1.5 |
| Cosmetic carrier (aqueous or aqueous-glycolic carrier) | ad 100 | ad 100 | ad 100 | ad 100 |

| | K21 | K22 | K23 | K24 |
|---|---|---|---|---|
| Emulsifier a) | 1.0 to 5.0 | 1.5 to 4.0 | 2.0 to 3.0 | 2.0 to 3.0 |
| Emulsifier b) | 0.5 to 3.5 | 0.7 to 3.0 | 0.8 to 2.0 | 0.8 to 1.5 |
| Weight ratio of emulsifier a):Emulsifier b) | 1.2:1 to 4.0:1 | 1.5:1 to 3.5:1 | 1.5:1 to 3.5:1 | 1.5:1 to 3.5:1 |
| Low-HLB emulsifier: ester of isostearic acid with propylene oxide | 0.1 to 1.7 | 0.2 to 1.5 | 0.3 to 1.2 | 0.4 to 1.0 |
| Emulsifier: hydrated castor oil with 20 to 60 EO | 0.1 to 4.0 | 0.2 to 3.0 | 0.3 to 2.0 | 0.5 to 1.5 |
| Deodorizing active ingredient c) | 0.0001 to 40 | 0.2 to 20 | 1.0 to 15 | 1.5 to 5.0 |
| Oil component d) | 0.1 to 5.0 | 0.3 to 4.0 | 0.5 to 3.0 | 0.6 to 1.5 |

| | | | | |
|---|---|---|---|---|
| Thickener* | 0.2 to 4.0 | 0.5 to 3.0 | 0.6 to 2.0 | 0.7 to 1.5 |
| Cosmetic carrier (aqueous or aqueous-glycolic carrier) | ad 100 | ad 100 | ad 100 | ad 100 |

| | K25 | K26 | K27 | K28 |
|---|---|---|---|---|
| Emulsifier a) isoceteth-20 | 1.0 to 5.0 | 1.5 to 4.0 | 2.0 to 3.0 | 2.0 to 3.0 |
| Emulsifier b) oleth-20 | 0.5 to 3.5 | 0.7 to 3.0 | 0.8 to 2.0 | 0.8 to 1.5 |
| Weight ratio of emulsifier a):Emulsifier b) | 1.2:1 to 4.0:1 | 1.5:1 to 3.5:1 | 1.5:1 to 3.5:1 | 1.5:1 to 3.5:1 |
| Low-HLB emulsifier: propylene glycol isostearate | 0.1 to 1.7 | 0.2 to 1.5 | 0.3 to 1.2 | 0.4 to 1.0 |
| PEG-40 Hydrogenated Castor Oil | 0.1 to 4.0 | 0.2 to 3.0 | 0.3 to 2.0 | 0.5 to 1.5 |
| Antiperspirant active ingredient c): aluminum chlorohydrate and/or aluminum sesquichlorohydrate | 2.0 to 40 | 5.0 to 30 | 8.0 to 25 | 10 to 20 |
| Oil component d), preferably isopropylisostearate | 0.1 to 5.0 | 0.3 to 4.0 | 0.5 to 3.0 | 0.6 to 1.5 |
| PEG-150-Distearate and/or PEG-150-Dioleate and/or a copolymer of trimethylhexane diisocyanate (TMHDI) and polyethylene glycol with 90 ethylene oxide units, terminally modified with a branched $C_{16}$-$C_{20}$ alcohol | 0.2 to 4.0 | 0.5 to 3.0 | 0.6 to 2.0 | 0.7 to 1.5 |
| Cosmetic carrier (aqueous or aqueous-glycolic carrier) | ad 100 | ad 100 | ad 100 | ad 100 |

| | K29 | K30 | K31 | K32 |
|---|---|---|---|---|
| Emulsifier a) isoceteth-20 | 1.0 to 5.0 | 1.5 to 4.0 | 2.0 to 3.0 | 2.0 to 3.0 |
| Emulsifier b) oleth-20 | 0.5 to 3.5 | 0.7 to 3.0 | 0.8 to 2.0 | 0.8 to 1.5 |
| Weight ratio of emulsifier a):Emulsifier b) | 1.2:1 to 4.0:1 | 1.5:1 to 3.5:1 | 1.5:1 to 3.5:1 | 1.5:1 to 3.5:1 |
| Low-HLB emulsifier: propylene glycol isostearate | 0.1 to 1.7 | 0.2 to 1.5 | 0.3 to 1.2 | 0.4 to 1.0 |
| PEG-40 Hydrogenated Castor Oil | 0.1 to 4.0 | 0.2 to 3.0 | 0.3 to 2.0 | 0.5 to 1.5 |
| Deodorizing active ingredient c) | 0.0001 to 40 | 0.2 to 20 | 1.0 to 15 | 1.5 to 5.0 |
| Oil component d), preferably isopropylisostearate | 0.1 to 5.0 | 0.3 to 4.0 | 0.5 to 3.0 | 0.6 to 1.5 |
| PEG-150-Distearate and/or PEG-150-Dioleate and/or a copolymer of trimethylhexane diisocyanate (TMHDI) and polyethylene glycol with 90 ethylene oxide units, terminally modified with a branched $C_{16}$-$C_{20}$ alcohol | 0.2 to 4.0 | 0.5 to 3.0 | 0.6 to 2.0 | 0.7 to 1.5 |
| Cosmetic carrier (aqueous or aqueous-glycolic carrier) | ad 100 | ad 100 | ad 100 | ad 100 |

*Thickener: in particular polyethylene glycol ethers of the general formula R—O—(—CH$_2$—CH$_2$—O—)$_n$—R', wherein R and R' independently denote branched or unbranched alkyl, aryl or alkenyl radicals and n is an integer greater than about 75, preferably an integer from about 100 to about 400, and particularly preferably an integer from about 120 to about 200, preferably PEG-150 Distearate and/or PEG-150 Dioleate; and/or at least one non-ionic polyurethane polymer, which comprises at least one polyurethane unit of the formula (Ib) and/or the formula (Ic), at least one nonionic polyether unit of the formula (IIa) and at least one ether unit of the formula (IIIb),

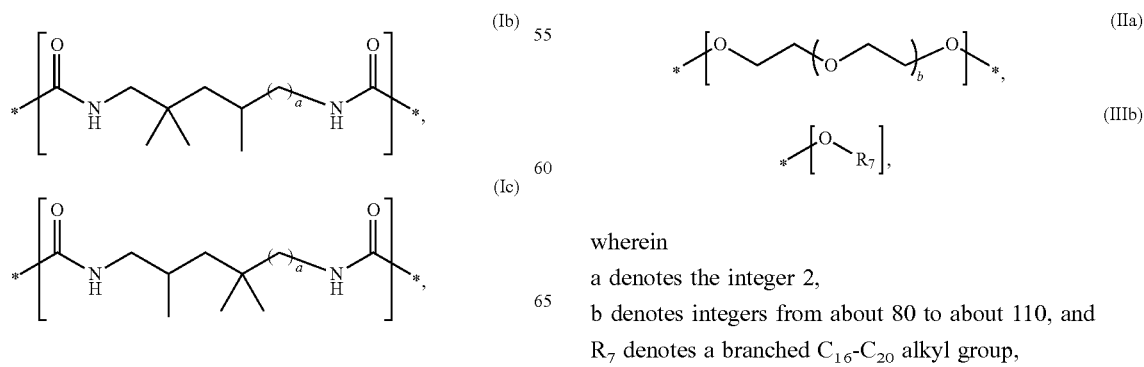

wherein a denotes the integer 2, b denotes integers from about 80 to about 110, and $R_7$ denotes a branched $C_{16}$-$C_{20}$ alkyl group, preferably a copolymer of trimethylhexane diisocyanate (TMHDI) and polyethylene glycol with about 90 ethylene oxide units, terminally modified with a branched $C_{16}$-$C_{20}$-alcohol.

Another subject matter of the present disclosure is a non-therapeutic cosmetic method for reducing the perspiration of the body and/or for reducing the body odor released by perspiration, wherein a cosmetic agent as contemplated herein or a preferred cosmetic agent as contemplated herein is applied to the human skin and remains on the application point for at least about 1 hour.

With respect to additional preferred embodiments of the subject method, particularly with regard to the cosmetic agents use there, the statements made about the cosmetic agents as contemplated herein apply mutatis mutandis.

The following examples explain the present disclosure without limiting it.

EXAMPLES

The quantities below are specified in wt. %, relative to the total weight of the cosmetic agents as contemplated herein.

According to the proportions specified in the table, antiperspirant microemulsions were produced, containing isoceteth-20 (emulsifier a)) and oleth-20 (emulsifier b)) as O/W emulsifiers, 1.0 wt. % propylenglycolmonoisostearate, 1.0 wt. % isopropylisostearate, 2.0 wt. % 1,2-propanediol, 13.4 wt. % aluminum chlorohydrate (active substance content), 1.2 wt. % PEG-150 Distearate, 1.0 wt. % perfume oil and 76.8 wt. % water.

The total quantities of isoceteth-20 and oleth-20 were each 3.6 wt. % in examples V1 and E1 and 3.3 wt.-% in example E2.

The oil-soluble constituents were placed in a closed charging vessel, stirred and heated up to 70° C. The water and aluminum chlorohydrate were placed in a further closed charging vessel, stirred and heated up to 70° C. As soon as the aqueous solution reached a temperature of 70° C., it was slowly added to the oil phase. The mixture was then stirred and cooled to room temperature.

The optical transmission Tz of the produced preparations was then photometrically determined. The table shows that the combination of the two O/W emulsifiers already leads to an improved transmission (V3 in comparison with V1 and V2). In the examples as contemplated herein with a surplus of isoceteth-20 (emulsifier a)) over oleth-20 (emulsifier b)) with a weight ratio of 3.5:1 (E1) or 1.5:1, the transmission values are greatly improved.

The results are shown in table 1 below.

TABLE 1

|   | O/W emulsifier combination | Weight ratio isoceteth-20:oleth-20 | Transmission Tz |
|---|---|---|---|
| V1 | 0 wt. % isoceteth-20 (emulsifier a)) 3.6 wt. % oleth-20 (emulsifier b)) | 0:3.6 | 63% |
| V2 | 3.6 wt. % isoceteth-20 (emulsifier a)) 0 wt. % oleth-20 (emulsifier b)) | 3.6:0 | 59% |
| V3 | 1.3 wt. % isoceteth-20 (emulsifier a)) 2.3 wt. % oleth-20 (emulsifier b)) | 0.56:1 | 71% |
| E1 | 2.8 wt. % isoceteth-20 (emulsifier a)) 0.8 wt. % oleth-20 (emulsifier b)) | 3.5:1 | 98% |
| E2 | 2.0 wt. % isoceteth-20 (emulsifier a)) 1.3 wt. % oleth-20 (emulsifier b)) | 1.54:1 | 100% |

The transparency was determined using a LICO 400 (long) at 22° C. and with a light wavelength of 500 nm.

Furthermore, the following antiperspirant cosmetic agents shown in table 2 were produced in the same way as described above:

TABLE 2

| Example: Raw material | 1 | 2 | 3 | 4 | 5 | 6 |
|---|---|---|---|---|---|---|
| Isoceteth-20 (Brij IC20N), Croda) | 2.8 | 2.0 | 2.8 | 2.8 | 2.0 | 2.8 |
| Oleth-20 (Brij O20, Croda) | 1.2 | 1.3 | 0.8 | 1.2 | 1.3 | 0.8 |
| Isopropyl isostearate (Crodamol IPIS, Croda) | 1.0 | 1.0 | 1.0 | 1.0 | 1.0 | 1.0 |
| PEG-40 Hydrated Castor Oil | 1.0 | 1.0 | 1.0 | 1.0 | 1.0 | 1.0 |
| Propylene glycol mono-isostearate (Cithrol PGMIS, Croda) | 0.5 | 1.0 | 1.0 | 1.0 | 1.0 | 1.0 |
| 1,2-propanediol | 1.2 | 1.2 | 1.2 | 1.2 | 1.2 | 1.2 |
| Aluminum chlorohydrate (50% in water, Locron L, Clariant) | — | — | — | 26.8 | 26.8 | 26.8 |
| Aluminum sesquichloro-hydrate (40% in water, Reach 301L, SummitReheis) | 25.0 | 25.0 | 25.0 | — | — | — |
| Phenoxyethanol | 0.9 | 0.9 | 0.9 | 0.9 | 0.9 | 0.9 |
| Benzalkonium chloride (50% in water, Barquat DM-50) | 0.2 | 0.2 | 0.2 | 0.2 | 0.2 | 0.2 |
| PEG-150 Distearate (Eumulgin EO33, BASF) | 1.2 | 1.2 | — | 1.2 | 1.2 | 1.2 |
| Rheoluxe 880 (Elementis) (INCI: Propylene glycol, Bis-$C_{16-20}$ isoalkoxy TMHDI/PEG-90 Copolymer, aqua (water)) | — | — | 3.0 | — | — | — |
| Perfume | 1.0 | 1.0 | 1.0 | 1.0 | 1.0 | 1.0 |
| Water | ad 100 | ad 100 | ad 100 | ad 100 | ad 100 | ad 100 |

Emulsions with a clear appearance were obtained at 22° C. The viscosity of the produced example compositions was in the range of 1200 to 2500 cps (20° C., Brookfield DV-II+ Pro, Spindle 3, 20 rpm).

The cosmetic agents thus produced in the form of transparent O/W emulsions have a high storage stability despite the low emulsifier content, even under fluctuating temperatures, and demonstrated excellent skin tolerance. Furthermore, the application of this agent leads to a high antiperspirant and/or deodorizing performance and a low residue formation on textiles. Furthermore, these agents have good usability and dosability.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. Cosmetic agent in the form of an O/W emulsion, comprising, in an aqueous cosmetically compatible carrier:
   polyoxyethylene (20) isocetyl ether present in an amount of from 2 to 2.8 wt. %, relative to the total weight of the cosmetic agent,
   polyoxyethylene (20) oleyl ether present in an amount of from 0.8 to 1.3 wt. %, relative to the total weight of the cosmetic agent,
   isopropyl isostearate present in an amount of 1 wt. %, relative to the total weight of the cosmetic agent,
   a hydrated castor oil with about 40 of ethylene oxide per mol of hydrated castor oil and present in an amount of 1 wt. %, relative to the total weight of the cosmetic agent,
   propylene glycol monoisostearate present in an amount of from 0.5 to 1 wt. %, relative to the total weight of the cosmetic agent,
   1,2-propanediol present in an amount of 1.2 wt. %, relative to the total weight of the cosmetic agent,
   aluminum chlorohydrate and/or aluminum sesquichlorohydrate present in an amount of from 10 to about 13.5 wt. %, relative to the total weight of the cosmetic agent,
   phenoxyethanol present in an amount of 0.9 wt. %, relative to the total weight of the cosmetic agent,
   benzalkonium chloride present in an amount of 0.1 wt. %, relative to the total weight of the cosmetic agent,
   polyethylene glycol-150 distearate present in an amount of from 0 to 1.2 wt. %, relative to the total weight of the cosmetic agent,
   propylene glycol, Bis-$C_{16-20}$ isoalkoxy TMHDI/PEG-90 copolymer, aqua present in an amount of from 0 to 3 wt. %, relative to the total weight of the cosmetic agent, and
   water,
   wherein the agent has a viscosity of from about 1200 to about 2500 cps (20° C., Brookfield, Spindle 3, 20 rpm) and
   wherein the agent has a transparency of at least 98% as determined using a LICO 400 (long) at 22° C. and with a light wavelength of 500 nm.

2. Cosmetic agent according to claim 1, wherein the propylene glycol, Bis-$C_{16-20}$ isoalkoxy TMHDI/PEG-90 Copolymer, aqua is present in an amount of 3 wt. %, relative to the total weight of the cosmetic agent and said cosmetic agent is free of the polyethylene glycol-150 Distearate.

3. Cosmetic agent according to claim 1, wherein the polyethylene glycol-150 Distearate is present in an amount of 1.2 wt. %, relative to the total weight of the cosmetic agent and said cosmetic agent is free of the propylene glycol, Bis-$C_{16-20}$ isoalkoxy TMHDI/PEG-90 Copolymer, aqua.

4. Cosmetic agent according to claim 1, wherein the polyoxyethylene (20) isocetyl ether is present in an amount of 2.8 wt. %, relative to the total weight of the cosmetic agent and the polyoxyethylene (20) oleyl ether present in an amount of 1.2 wt. %, relative to the total weight of the cosmetic agent, and the agent has a transparency of at least 98% as determined using a LICO 400 (long) at 22° C. and with a light wavelength of 500 nm.

5. Cosmetic agent according to claim 1, wherein the polyoxyethylene (20) isocetyl ether is present in an amount of 2 wt. %, relative to the total weight of the cosmetic agent and the polyoxyethylene (20) oleyl ether present in an amount of 1.3 wt. %, relative to the total weight of the cosmetic agent, and the agent has a transparency of about 100 as determined using a LICO 400 (long) at 22° C. and with a light wavelength of 500 nm.

6. Cosmetic agent according to claim 1, wherein the polyoxyethylene (20) isocetyl ether is present in an amount of 2 wt. %, relative to the total weight of the cosmetic agent.

7. Cosmetic agent according to claim 1, wherein the polyoxyethylene (20) isocetyl ether is present in an amount of 2.8 wt. %, relative to the total weight of the cosmetic agent.

8. Cosmetic agent according to claim 1, wherein the polyoxyethylene (20) oleyl ether is present in an amount of 0.8 wt. %, relative to the total weight of the cosmetic agent.

9. Cosmetic agent according to claim 1, wherein the polyoxyethylene (20) oleyl ether is present in an amount of 1.3 wt. %, relative to the total weight of the cosmetic agent.

10. Cosmetic agent according to claim 1, wherein the polyethylene glycol-150 distearate is present in an amount of about 0 wt. %, relative to the total weight of the cosmetic agent, and the propylene glycol, Bis-$C_{16-20}$ isoalkoxy TMHDI/PEG-90 copolymer, aqua present is present in an amount of about 0 wt. %, relative to the total weight of the cosmetic agent.

11. Cosmetic agent in the form of an O/W emulsion, comprising, in an aqueous cosmetically compatible carrier:
   a) polyoxyethylene (20) isocetyl ether present in an amount of from 2 to 2.8 wt. %, relative to the total weight of the cosmetic agent,
   b) polyoxyethylene (20) oleyl ether present in an amount of from 0.8 to 1.3 wt. %, relative to the total weight of the cosmetic agent,
   c) at least one antiperspirant and/or deodorizing active ingredient, and
   d) at least one oil component;
   wherein the total quantity of emulsifiers in the cosmetic agent is from about 1.5 to about 8.0 wt. %, relative to the total weight of the cosmetic agent,
   the weight ratio of the non-ionic emulsifier a) to the non-ionic emulsifier b) is from about 1.5:1 to about 3.5:1;
   wherein the agent has a viscosity of from about 1200 to about 2500 cps (20° C., Brookfield, Spindle 3, 20 rpm) and
   wherein the agent has a transparency of at least 98% as determined using a LICO 400 (long) at 22° C. and with a light wavelength of 500 nm.

12. Cosmetic agent according to claim 11, wherein the polyoxyethylene (20) isocetyl ether is present in an amount of 2.8 wt. %, relative to the total weight of the cosmetic agent and the polyoxyethylene (20) oleyl ether present in an amount of 0.8 wt. %, relative to the total weight of the cosmetic agent.

13. Cosmetic agent according to claim 11, wherein the polyoxyethylene (20) isocetyl ether is present in an amount of 2 wt. %, relative to the total weight of the cosmetic agent and the polyoxyethylene (20) oleyl ether present in an amount of 1.3 wt. %, relative to the total weight of the cosmetic agent, and the agent has a transparency of about 100% as determined using a LICO 400 (long) at 22° C. and with a light wavelength of 500 nm.

14. Cosmetic agent according to claim 11, wherein the polyoxyethylene (20) isocetyl ether is present in an amount of 2 wt. %, relative to the total weight of the cosmetic agent.

15. Cosmetic agent according to claim 11, wherein the polyoxyethylene (20) isocetyl ether is present in an amount of 2.8 wt. %, relative to the total weight of the cosmetic agent.

16. Cosmetic agent according to claim 11, wherein the polyoxyethylene (20) oleyl ether is present in an amount of 0.8 wt. %, relative to the total weight of the cosmetic agent.

17. Cosmetic agent according to claim 11, wherein the polyoxyethylene (20) oleyl ether is present in an amount of 1.3 wt. %, relative to the total weight of the cosmetic agent.

18. Cosmetic agent according to claim 11, wherein the total quantity of emulsifiers is about 1.5 wt. %, relative to the total weight of the cosmetic agent.

19. Cosmetic agent according to claim 11, wherein the total quantity of emulsifiers is about 8 wt. %, relative to the total weight of the cosmetic agent.

20. Cosmetic agent according to claim 11, wherein the agent has a transparency of about 100% as determined using a LICO 400 (long) at 22° C. and with a light wavelength of 500 nm.

* * * * *